US00PP21617P2

(12) United States Plant Patent
Pan

(10) Patent No.: US PP21,617 P2
(45) Date of Patent: Jan. 11, 2011

(54) ***LANTANA* PLANT NAMED 'BANI YELBIC'**
(50) Latin Name: *Lantana camara L.*
Varietal Denomination: Bani Yelbic

(75) Inventor: Shifeng Pan, Hollister, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/589,363

(22) Filed: Oct. 22, 2009

(51) Int. Cl.
*A01H 5/00* (2006.01)

(52) U.S. Cl. ..... Plt./227
(58) Field of Classification Search ..... Plt./227
See application file for complete search history.

*Primary Examiner*—June Hwu
*Assistant Examiner*—Louanne C Krawczewicz Myers
(74) *Attorney, Agent, or Firm*—S. Matthew Edwards

(57) ABSTRACT

A new *Lantana* plant named 'Bani Yelbic,' particularly distinguished by the large sized, bright yellow flower color that matures to white, excellent floriferousness because of limited seed set, compact and dense mounding habit with dark green foliage.

1 Drawing Sheet

Latin name of the genus and species of the plant claimed: *Lantana camara L.*

Varietal denomination: 'Bani Yelbic'.

BACKGROUND OF THE NEW PLANT

The present invention comprises a new *Lantana,* botanically known as *Lantana camara L.* and hereinafter referred to by the variety name 'Bani Yelbic.'

'Bani Yelbic' is a product of a planned breeding program. The new cultivar 'Bani Yelbic' has large sized, bright yellow flower color that matures to white, excellent floriferousness because of limited seed set, compact and dense mounding habit with dark green foliage.

'Bani Yelbic' originates from a hybrid pollination in a controlled breeding program in Gilroy, Calif. The pollination was made in June 2006 and the seed sown in December 2006. The female parent was an unpatented, proprietary plant identified as '106-1' with white color. '106-1' has smaller flowers, lighter green foliage and a taller plant habit than 'Bani Yelbic.'

The male parent was an unpatented, proprietary plant identified as 'E36-2' with pink flowers, with is later to flower and has a taller plant habit.

'Bani Yelbic' was selected as one flowering plant within the progeny of the stated cross in April 2007 in a controlled environment in Gilroy, Calif.

The first act of asexual reproduction of 'Bani Yelbic' was accomplished when vegetative cuttings were propagated from the initial selection in the April 2007 in a controlled environment in Gilroy, Calif.

BRIEF SUMMARY OF INVENTION

Horticultural examination of plants grown from cuttings of the plant initiated in April, 2007 in Gilroy, Calif., and continuing thereafter, has demonstrated that the combination of characteristics as herein disclosed for 'Bani Yelbic' are firmly fixed and are retained through successive generations of asexual reproduction.

'Bani Yelbic' has not been observed under all possible environmental conditions. The phenotype may vary significantly with variations in environment such as temperature, light intensity and day length.

A Plant Breeder's Right for this cultivar was applied for in Canada on Jan. 30, 2009. 'Bani Yelbic' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawing shows typical flower and foliage characteristics of 'Bani Yelbic' with colors being as true as possible with an illustration of this type. The photographic drawing shows a flowering potted plant of the new variety growing in a 4.5 inch pot, and a close up of the flowers. These plants were grown outdoors in Gilroy, Calif. The plants were about 20-22 weeks of age when the photo was taken in July 2009.

DETAILED BOTANICAL DESCRIPTION

The plant descriptions, measurements and aforementioned photographs were taken in Gilroy, Calif. in April 2009 in a greenhouse. These plants were growing in 4.5 inch pots in a trial setting. The plants were about 16-18 weeks of age and were grown with several early sprays of Paclobutrazol, a plant growth regular.

Color Chart used: Royal Horticultural Society Colour Chart (R.H.S.) 2001.

TABLE 1

DIFFERENCES BETWEEN THE NEW VARIETY 'BANI YELBIC' AND A SIMILAR VARIETY

| | 'Bani Yelbic' | 'Simon Yellow' (Unpatented) |
|---|---|---|
| Flower size: | Larger | Smaller |
| Flowering response: | Earlier | Later |
| Plant habit: | More compact | Less compact |

Plant:
*Form, growth and habit.*—Semi-woody, grown as an annual or perennial; compact and dense mounding habit; well branched.
*Plant height.*—10-12 cm.
*Plant height* (*inflorescence included*).—11-13 cm.
*Plant width.*—18-20 cm.

Foliage:
*Type.*—Opposite.
*Immature, leaf color, upper surface.*—Closest to RHS 137A.
*Lower surface.*—Closest to RHS 137C.
*Mature, leaf color, upper surface.*—Much darker than RHS 147A.
*Lower surface.*—Lighter than RHS 147A.
*Length.*—5.3-5.7 cm.
*Width.*—3.2-3.3 cm.
*Shape.*—Ovate.
*Base shape.*—Attenuate.
*Apex shape.*—Acute.
*Margin.*—Denticulate to slightly serrulate.
*Texture, upper surface.*—Hirsute, glandular hairs.
*Lower surface.*—Hirsute, glandular hairs.
*Color of veins.*—Both surfaces; RHS 144A basally, otherwise indistinct.
*Petioles color.*—RHS 144A.
*Petioles length.*—1.2-1.4 cm.
*Diameter of petiole.*—0.2 cm.
*Texture.*—Hirsute, pilose, and a few glandular hairs.

Stem:
*Quantity of main branches per plant.*—4-5.
*Quantity of leaves per branch.*—8-10.
*Color of stem.*—Between RHS 144A and RHS 144B.
*Length of stem.*—10-12 cm.
*Diameter.*—0.2 cm.
*Length of internodes.*—0.5-2.0 cm.
*Texture.*—Pilose, and a few glandular hairs.

Inflorescence:
*Type.*—Umbel like, flattened semi-sphere the florets are sessile on an ovate receptacle.
*Blooming habit.*—Flowers continuously from spring through fall.
*Number of flowers per inflorescence.*—About 30-35.
*Quantity of inflorescences per plant.*—20-25.
*Lastingness of individual blooms on the plant.*—About 4 weeks (depending on temperatures).
*Fragrance.*—Spicy.
*Umbel horizontal diameter.*—3.5-4.0 cm.
*Umbel vertical height.*—1.8 cm.
*Color of peduncle.*—Between RHS 144A and RHS 144B.
*Length of peduncle.*—2.3-3.0 cm.
*Peduncle diameter.*—0.15 cm.
*Texture.*—Hirsute, pilose, and glandular hairs.

Corolla:
*Form.*—Salver-shaped to shallow cup-shaped, with a relatively long tube at the base. Each floret subtended by a single bract.
*Floret horizontal diameter.*—0.9-1.0 cm.
*Floret depth.*—2.1 cm.
*Immature, color of petals, upper surface.*—Closest to RHS 14A.
*Lower surface.*—Closest to RHS 13C.
*Mature, color of petals, upper surface.*—Between RHS 6A and RHS 6B, maturing to RHS 155D.
*Lower surface.*—Closest to RHS 155D.
*Petal length.*—0.4-0.5 cm.
*Petal diameter.*—0.3-0.5 cm.
*Apex.*—Rounded.
*Margin.*—Entire.
*Shape.*—Obovate.
*Degree of lobation.*—Moderate.
*Texture, upper surface.*—Papillose.
*Lower surface.*—Papillose.
*Corolla tube, color, outer surface.*—RHS 155A.
*Inner surface.*—RHS 155A.
*Corolla tube length.*—1.1 cm.
*Diameter* (*at opening*).—0.1 cm.
*Corolla tube texture, outer surface.*—Slightly hirsute basally.
*Inner surface.*—Papillose.

Bud (just before opening):
*Color.*—RHS 17B.
*Length.*—1.1-1.3 cm.
*Width.*—0.2-0.3 cm at the apex.
*Shape.*—Tubular with a flared apex.

Bract:
*Color.*—RHS 144C with a RHS 144A apex.
*Length.*—0.4 cm.
*Diameter.*—0.15 cm.
*Texture, outer surface.*—Hirsute.
*Inner surface.*—Glandular hairs on the inner surface.

Calyx:
*Number of sepals.*—5, fused sepals forming a short tube around the base of each floret.
*Color of sepals.*—RHS 144D.
*Length of sepals.*—0.2 cm.
*Width of sepals.*—0.15 cm.
*Sepal shape.*—Tube-shaped with 2 short lobes.
*Apex shape.*—Obtuse.
*Texture, upper surface.*—Hirsute; glandular hairs.
*Lower surface* (*inside*).—Glabrous.

Reproductive organs:
*Pistil.*—1.
*Length.*—0.5 cm.
*Style color.*—RHS 155C.
*Style length.*—0.4 cm.
*Stigma color.*—RHS 144B to RHS 144C.
*Stamens.*—4.
*Color of filaments.*—RHS 155 C.
*Length filaments.*—0.6-0.7 cm.
*Anther color.*—RHS 14C.
*Length of anthers.*—0.1 cm.
*Anther shape.*—Oblong.
*Pollen amount.*—Sparse.
*Color of pollen.*—RHS 10C.

Disease/pest resistance: No disease/pest resistance has been observed on this hybrid.

What is claimed is:

1. A new and distinct variety of *Lantana* plant named 'Bani Yelbic,' substantially as illustrated and described herein.

* * * * *

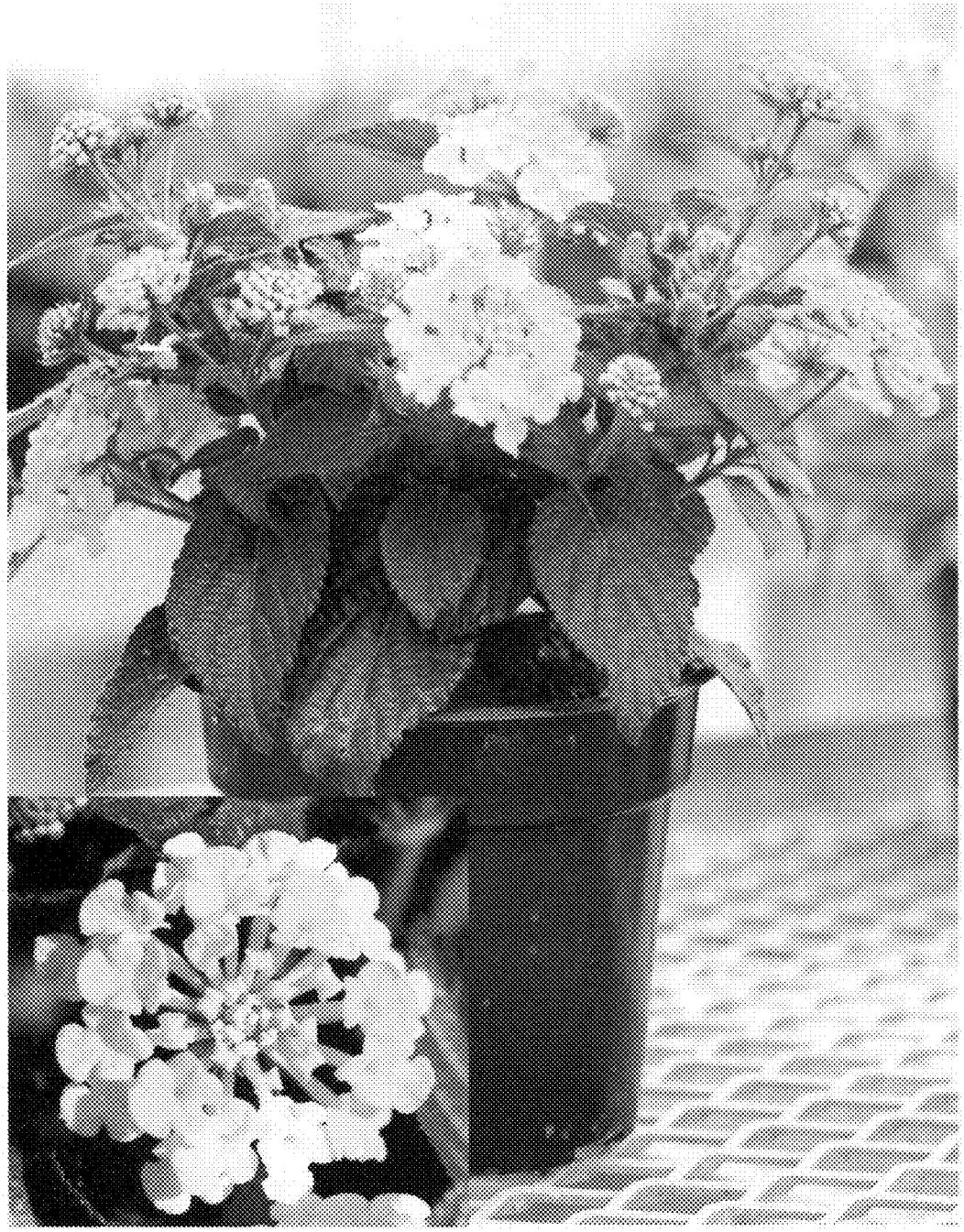

UNITED STATES PATENT AND TRADEMARK OFFICE

CERTIFICATE OF CORRECTION

PATENT NO. : PP21,617 P2
APPLICATION NO. : 12/589363
DATED : January 11, 2011
INVENTOR(S) : Pan It is certified that error appears in the above-identified patent and that said Letters Patent is hereby corrected as shown below:

On Title page, item [54], delete "BANI YELBIC" and insert therefor --'BAN YELBIC'--

On Title page, item [57], line 1, delete "Bani Yelbic" and insert therefor --'Ban Yelbic'--

In column 1, lines 3, 8, 9, 10, 14, 19, 23, 26, 36, and 39, delete "Bani Yelbic" and insert therefor --'Ban Yelbic'--

In column 2, lines 2, 13, and 37, delete "Bani Yelbic" and insert therefor --'Ban Yelbic'--

In column 2, in TABLE 1, at line 34, delete "BANI YELBIC" and insert therefor --'BAN YELBIC'--

In column 4, in claim 1, lines 59-60, delete "Bani Yelbic" and insert therefor --'Ban Yelbic'--

Signed and Sealed this
Twenty-ninth Day of January, 2013

David J. Kappos

David J. Kappos
*Director of the United States Patent and Trademark Office*